US00PP09709P

United States Patent [19]

Martin et al.

[11] Patent Number: Plant 9,709

[45] Date of Patent: Nov. 26, 1996

[54] AVOCADO TREE CALLED 'SIR-PRIZE'

[75] Inventors: Gray E. Martin, Moreno Valley; Berthold O. Bergh, Riverside, both of Calif.

[73] Assignee: The Regents of the University of California, Alameda, Calif.

[21] Appl. No.: 481,572

[22] Filed: Jun. 7, 1995

[51] Int. Cl.[6] ..... A01H 5/00

[52] U.S. Cl. ..... Plt./44

[58] Field of Search ..... Plt./44

[56] References Cited

U.S. PATENT DOCUMENTS

P.P. 139 8/1935 Hass ..... Plt./44

*Primary Examiner*—James R. Feyrer

*Attorney, Agent, or Firm*—Townsend and Townsend and Crew

[57] ABSTRACT

A new and distinct variety of avocado tree characterized by fruit similar to the 'Hass' industry standard but earlier-maturing and more productive. The new variety, due to its Mexican race genes, is more suitable than 'Hass' in colder growing areas. Season of maturity averages 6–8 weeks earlier than 'Hass' in any one location and overall fruit size is larger than 'Hass' making early-season maturity more important.

3 Drawing Sheets

DESCRIPTION

This invention relates to a new and distinct variety of avocado tree (*Persea americana*) designated as 'Sir-Prize' and tested as selection 4-18-5.

The 'Sir-Prize' mother tree was one of many seedlings which originated from a University of California open-pollinated breeding cross with the 'HX48' avocado selection as the maternal parent. The 'HX48' was a 'Hass' seedling and thus, 'Sir-Prize' can be described as a "grandchild" of 'Hass', which is the current dominant commercial variey in California and the world. 'Sir-Prize' has been asexually reproduced by the grafting of budwood onto rootstocks both in the nursery and in the field. 'Sir-Prize' was first asexually reproduced on the South Coast Research and Education Center, field 46, row 42, trees 21, 22 and 24 in June of 1991.

Figure 1:
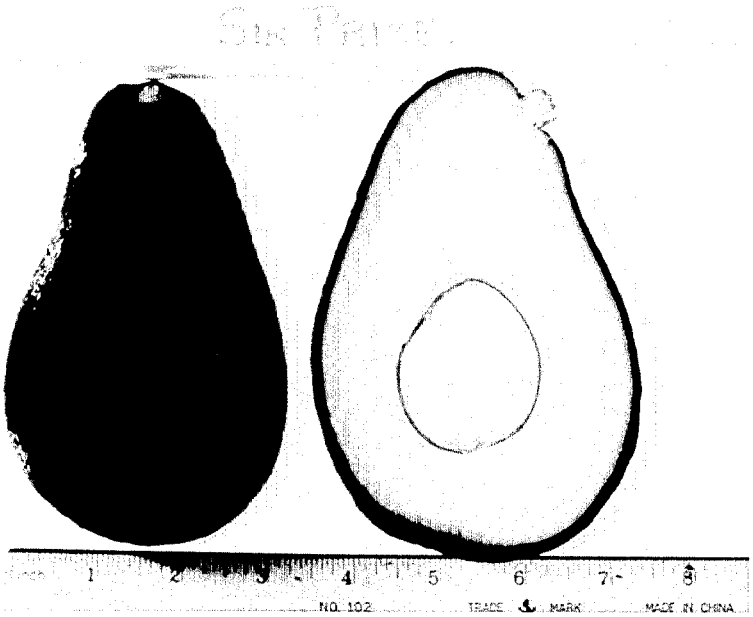
FIG. 1 shows a frontal and a side view of cut and uncut fruit of 'Sir-Prize' which is typical of the new variety.
Figure 2:
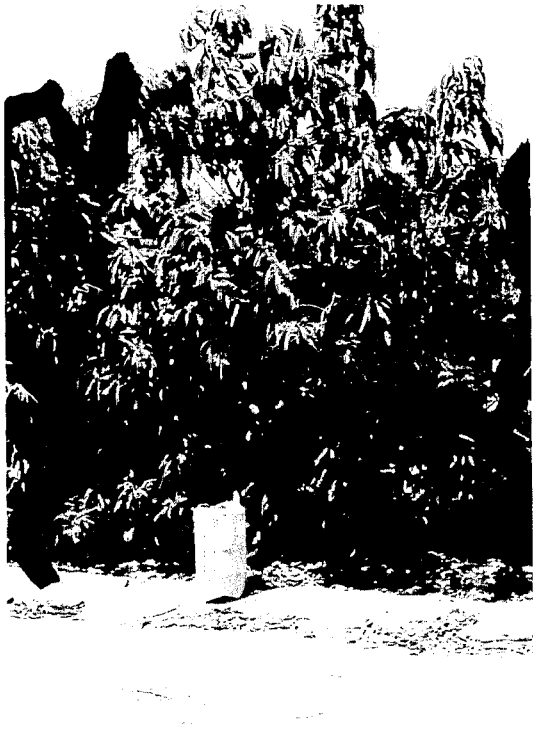
FIG. 2 illustrates a tree typical of the 'Sir-Prize' variety showing a more spreading and much more open tree than that of 'Hass'.
Figure 3:
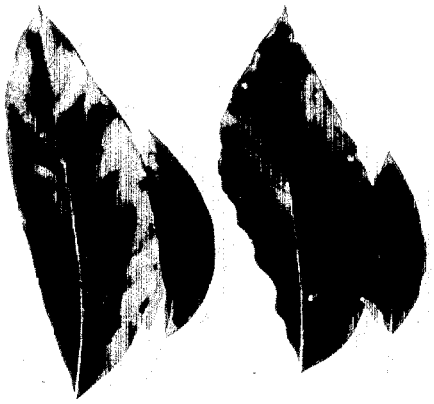
FIG. 3 illustrates a typical leaf of the 'Sir-Prize' variety compared with one of the 'Hass' variety and shows the wavier leaf margin of 'Sir-Prize'.
Figure 4:
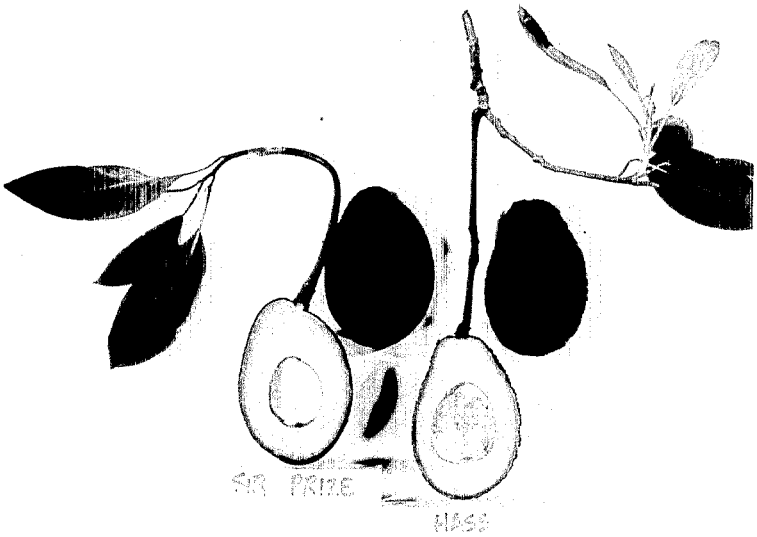
FIG. 4 illustrates a typical seed of the 'Sir-Prize' variety compared with that of 'Hass' having a smaller seed than'Hass' and more pear-shaped fruit.

'Sir-Prize' has several distinguishing characteristics which make it commercially valuable. One is its appearance. Although the appearance of 'Sir-Prize' is significantly different from 'Hass', it is more 'Hass'-like than any previous commercial avocado of its type. When ripe, both the black color of the skin and the pear shape of the fruit will lead most consumers to recognize it as 'Hass' or at least as a 'Hass'-type. Another important characteristic is the season of maturity of the new variety which averages 6–8 weeks earlier than 'Hass' in any one location. Also, the overall fruit size of 'Sir-Prize' is larger than 'Hass', and size increase occurs earlier in the season, making early-season maturity even more important. Currently, large-sized, early-season, 'Hass'-type avocados like 'Sir-Prize' command premium returns to growers. 'Sir-Prize' is primarily classified as a Mexican-race type avocado. Mexican-race avocados are typically more cold-resistant and are, therefore, selected for growing in inland valleys and other regions otherwise unsuitable for 'Hass'. With 'Sir-Prize', avocado growers in California's central San Joaquin valley, which is unsuited for growing 'Hass', will have the opportunity of growing a 'Hass'-type avocado.

Early producion data indicate a heavy yield potential. Unfortunately, the time required to statistically document yield is approximately six years from early completion. The flower type of 'Sir-Prize' is 'B', the compliment of 'A' ('Hass'). Commonly avocados of the 'B'-type are used for enhancing pollination affect and increasing yield for 'Hass'. Accordingly, in addition to its other benefits, 'Sir-Prize' shows promise as a high-quality saleable pollinator.

SPECIFIC DESCRIPTION

Fruit

The fruit shape is pear with a distinctive ridge along one side. The extent of the ridge is slight to moderate and becomes almost unrecognizable as the fruit loses moisture during the ripening process. The unripe green fruit color, with reference to the Horticulture Colour Charts, (issued by Wilson Colour Ltd., in collaboration with The Royal Horticulture Society) designates the typical fruit of 'Sir-Prize' as having a background skin color which is spinach green, 00960 (Repertoire, Vert Epinard 270/4). The fruit size is significantly larger than'Hass', averaging greater than 350 grams on juvenile trees. This large size is recognized as favorable in the early-season market period. The skin texture is a medium-minus, and not truly pebbled like 'Hass'. The skin is flecked with numerous tiny islands of varying yellowish shades, giving the illusion of 'Hass'-like pebbles. The skin thickness is fine-plus, similar to the commercial variety 'Fuerte'. This skin thickness is commonly referred to as "thin" as compared with the "thick" skin of 'Hass'. The skin is pliable and separates easily from the flesh. The flesh color is similar to and indistinguishable from 'Hass'. Flesh fibers are few and insignificant. The seed size is desribed as "small", with an average seed-to-fruit ratio of 10–12%; comparable 'Hass' ratios average 15% or higher. The flesh quality is considered excellent, equivalent with 'Hass'; exceeding 'Hass' during the early-season period. Preliminary postharvest handling features appear promising and should be "more than acceptable."

In flavor the variety is rated "very good, rich" and about the same as 'Hass'. In oil content, initial data indicate that the variety will have peak dry matter considerably earlier than 'Hass' because of its earlier maturation but at a lower level than the 'Hass' peak. However, the variety has not had a true comparison of dry matter with 'Hass' to date.

Tree and Foliage

Individual differences in tree form and leaf foliage are frequently subtle and generally nondescriptive. 'Sir-Prize' is upright in tree form, although this character can be influenced by pruning. The leaf type and shape is more typical of the Mexican race avocados than 'Hass'. Young leaf anthocyanin pigment is present varying from light to moderate. No anise fragrance has been detected in the stems or leaves. This leaf margin of variety is wavier than that of 'Hass'. Avocado leaf color varies widely with leaf age, location on the tree, light exposure and individual nutrition. For this variety a typical immature leaf would be lettuce green (861/2) and commonly has a reddish-brown overlay. For mature leaves, the leaves of the variety average spinach green (000960). Leaf shape is elliptical to slightly ovate, with acute tips. The variety has acute bases whereas 'Hass' is slightly more obtuse. Inflorescences are not notably different between this variety and 'Hass'. Pedicels ("fruit stalks") are cylindrical to slightly conical, with no "nail head" flange at the point of fruit attachment. The average pedicel length and width is 10×1 cm. The pedicel point of attachment is slightly off-center, opposite the dominant ridge characteristic of 'Sir-Prize'. Peak bloom pepriod is earlier than 'Hass' by several weeks, the flower type is 'B'. Fruit set frequently occurs in clusters with production occurring throughout the tree. Fruit set appears more regular, less alternate, then 'Hass'.

Fruit stems are exceptionally shorter than the average stems of 'Hass' and most other avocado varieties, namely about 10 cm or a bit longer. Otherwise, stems are similar to 'Hass'. In the drawing only the stub of the stem is depicted because the rest of the stem has been cut off as is normally done with commercial fruits. Fruits of 'Sir-Prize' become deeper green as they develop and are spinach green (000960) at maturity, close to the color of a mature 'Hass' leaf. Produce is commonly geen when picked; unlike other commercial California avocados, the fruit skin turns black as it ripens to edible softness. Fruit shape varies in all avocados with distance from the ocean and from fruit to fruit on a given tree. This variety will have overlapping fruit shapes. Fruit size also overlaps with 'Hass'. Combining this with the black ripe skin color, the fruit of the variety will be able to capitalize on the excellent market recognition of the 'Hass' variety which is now dominant in the industry. The tree of the variety is a vigorous grower similar to 'Hass' and more so than its parent 'H×48'. Under conditions where the 'Hass' trees might have a height and spread of 8 m each, 'Sir-Prize' has a height and spread of 8 m by 5 m. Branching of 'Sir-Prize' is quite similar to 'Hass' including major scaffolds. Bark is also not discriminative. Water sprouts are not a phenomenon of normal healthy avocado trees. Leaf shape of 'Sir-Prize', as in the case of 'Hass', is elliptical to slightly ovate, with acute tips. 'Sir-Prize' has acute bases whereas 'Hass' is slightly more obtuse. The precocity and productivity of the tree ont he basis of 1955 production results, in comparison with 'Hass' indicated that 'Sir-Prize' bears at least as well as 'Hass', is significantly earlier-maturing and probably more cold hardy. Excessive pruning does not induce wild branching.

We claim:

1. The new and distinct variety of Avocado Tree herein described and illustrated and identified by the characteristics enumerated above.

* * * * *